US 12,059,826 B2

(12) United States Patent
Hedhammar et al.

(10) Patent No.: US 12,059,826 B2
(45) Date of Patent: Aug. 13, 2024

(54) STRUCTURING OF SURFACE-ACTIVE MACROMOLECULES

(71) Applicant: SPIBER TECHNOLOGIES AB, Stockholm (SE)

(72) Inventors: My Hedhammar, Stockholm (SE); Linnea Gustafsson, Stockholm (SE); Ronnie Jansson, Stockholm (SE); Wouter van der Wijngaart, Stockholm (SE)

(73) Assignee: SPIBER TECHNOLOGIES AB, Stockholm (SE)

( * ) Notice: Subject to any disclaimer, the term of this patent is extended or adjusted under 35 U.S.C. 154(b) by 1176 days.

(21) Appl. No.: 16/644,772

(22) PCT Filed: Sep. 26, 2018

(86) PCT No.: PCT/EP2018/076066
§ 371 (c)(1),
(2) Date: Mar. 5, 2020

(87) PCT Pub. No.: WO2019/063590
PCT Pub. Date: Apr. 4, 2019

(65) Prior Publication Data
US 2021/0069939 A1 Mar. 11, 2021

(30) Foreign Application Priority Data
Sep. 26, 2017 (EP) .................................. 17193218

(51) Int. Cl.
*B82Y 40/00* (2011.01)
*B29C 33/42* (2006.01)
(Continued)

(52) U.S. Cl.
CPC .......... *B29C 39/026* (2013.01); *B29C 33/424* (2013.01); *B29C 39/10* (2013.01);
(Continued)

(58) Field of Classification Search
CPC .......... B29C 41/12; B82Y 40/00; B82Y 30/00
See application file for complete search history.

(56) References Cited

U.S. PATENT DOCUMENTS

2018/0166289 A1* 6/2018 Kim ........................ B32B 33/00
2019/0002510 A1* 1/2019 Ittah ................. C07K 14/43518
(Continued)

FOREIGN PATENT DOCUMENTS

JP 2003-286100 A 10/2003
JP 2008-506409 A 3/2008
(Continued)

OTHER PUBLICATIONS

European Search and Examination Report for European Patent Application No. 17193218.9, dated Oct. 31, 2017.
(Continued)

*Primary Examiner* — S. Behrooz Ghorishi
*Assistant Examiner* — Alexander A Wang
(74) *Attorney, Agent, or Firm* — LATHROP GPM LLP; James H. Velema, Esq.

(57) ABSTRACT

A method for manufacturing shaped polymers of surface-active macromolecules, in particular silk, is provided. The method is comprising the steps of: • a) depositing an aqueous solution of the surface-active macromolecules on a surface, wherein the aqueous solution of the surface-active macromolecules is deposited in the form of a droplet, and wherein the surface is a hydrophobic micropatterned surface adapted to prevent the aqueous solution from penetrating into the pattern and to receive the droplet of the aqueous solution of the surface-active macromolecules and retain its droplet state; and • b) forming shaped polymers of the surface-active macromolecules on the surface.

24 Claims, 4 Drawing Sheets
Specification includes a Sequence Listing.

(51) Int. Cl.
   B29C 39/02    (2006.01)
   B29C 39/10    (2006.01)
   B29C 41/12    (2006.01)
   C07K 14/435   (2006.01)
   C09D 127/12   (2006.01)
   B82Y 30/00    (2011.01)

(52) U.S. Cl.
   CPC ........ B29C 41/12 (2013.01); C07K 14/43518 (2013.01); C09D 127/12 (2013.01); B82Y 30/00 (2013.01); B82Y 40/00 (2013.01)

(56) References Cited

U.S. PATENT DOCUMENTS

| 2019/0031843 | A1 | 1/2019 | Numata et al. |
| 2020/0069845 | A1* | 3/2020 | Omenetto ............... A61L 27/52 |

FOREIGN PATENT DOCUMENTS

| JP | 2013-512773 A | 4/2013 |
| KR | 10-2009-0023365 A | 3/2009 |
| WO | WO 2006/008163 A2 | 1/2006 |
| WO | WO 2007/016524 A2 | 2/2007 |
| WO | WO 2007/128378 A1 | 11/2007 |
| WO | WO 2011/069643 A2 | 6/2011 |
| WO | WO 2017/025964 A1 | 6/2011 |
| WO | WO 2017/131196 A1 | 8/2017 |

OTHER PUBLICATIONS

Gomes et al., "Antimicrobial functionalized genetically engineered spider silk", Biomaterials, Feb. 19, 2011, 32(18): 4255-4266.

International Search Report and Written opinion for PCT International Patent Application No. PCT/EP2018/076066, mailed Nov. 26, 2018.

Jung et al., "Wetting behaviour during evaporation and condensation of water microdroplets on superhydrophobic patterned surfaces", Journal of Microscopy, Dec. 7, 2007, 229(1): 127-140.

Shen et al., "Cross-plane thermal transport in micrometer-thick spider silk films", Polymer, Apr. 1, 2014, 55(7): 1845-1853.

Tsioris et al., "The Effect of Hydrophobic Patterning on Micromolding of Aqueous-Derived Silk Structures", MRS Proceedings, Jan. 1, 2007, 1052: 1-7.

\* cited by examiner

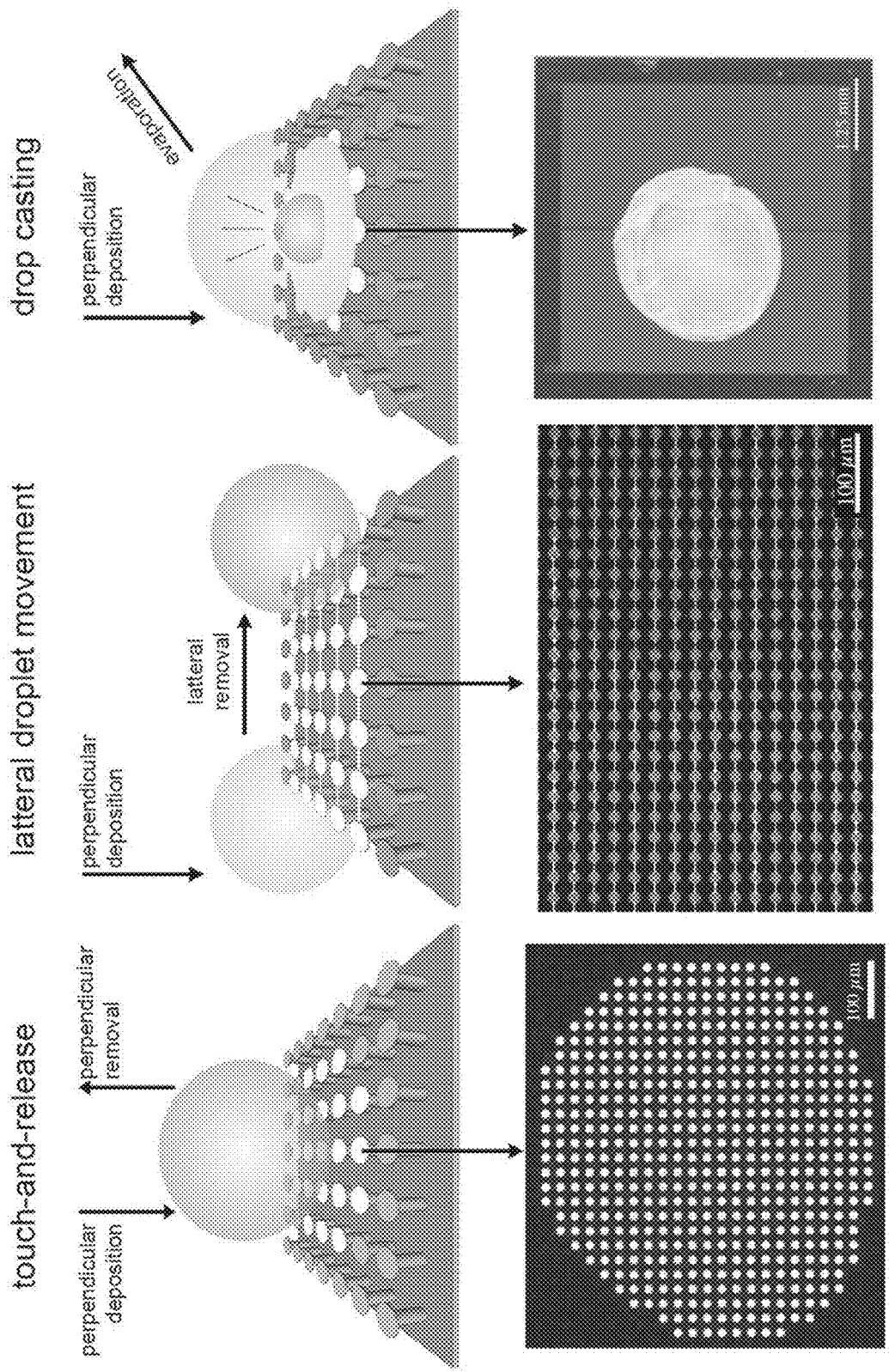

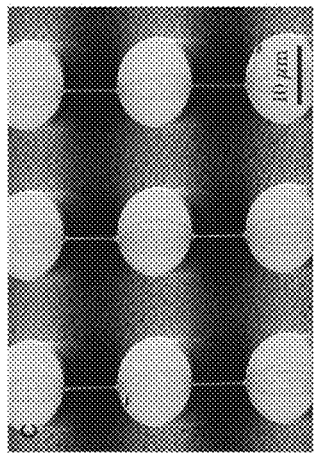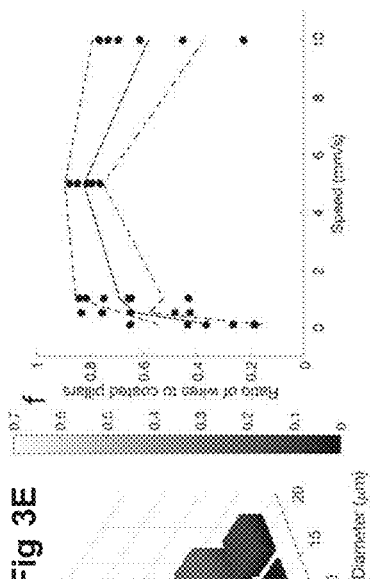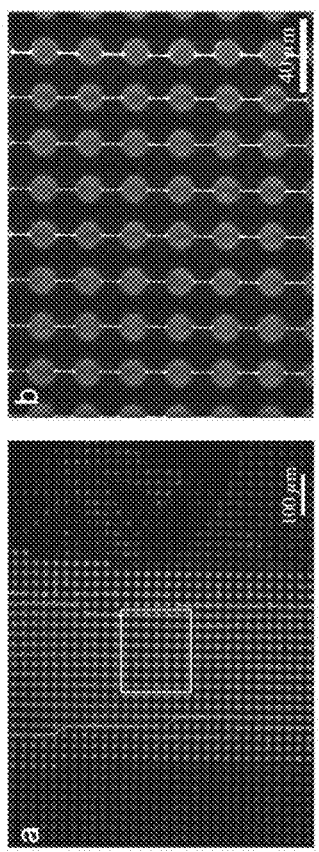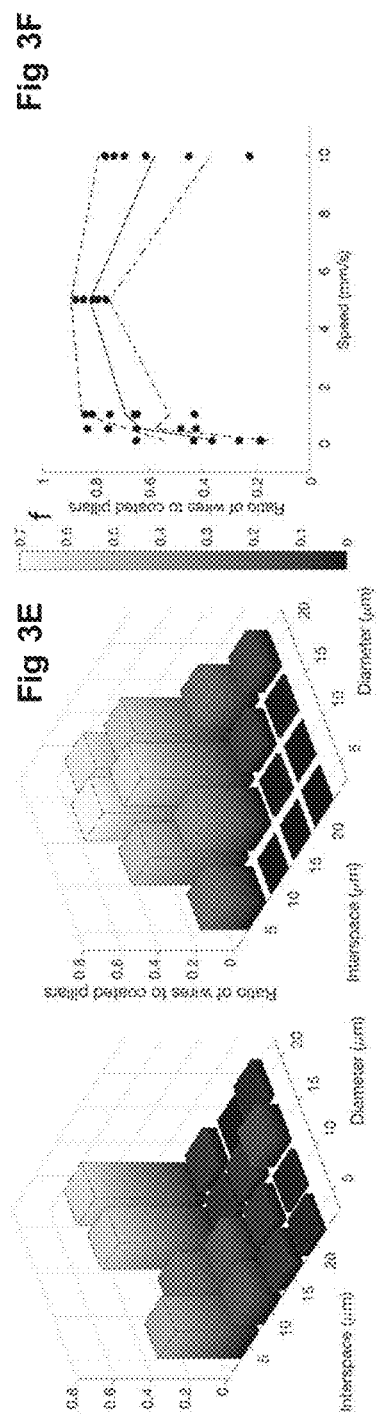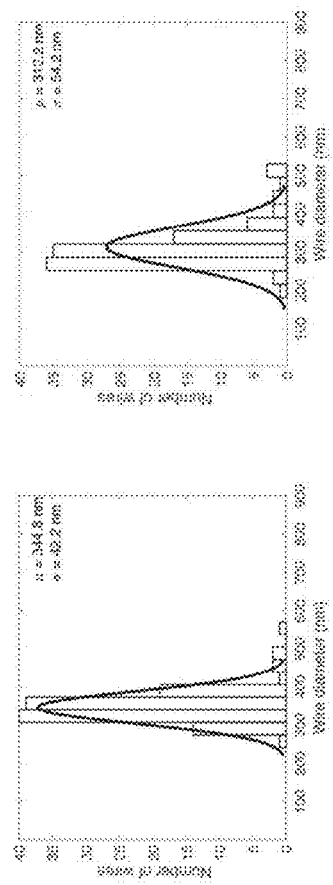

STRUCTURING OF SURFACE-ACTIVE MACROMOLECULES

RELATED APPLICATIONS

This application is a 35 U.S.C. § 371 filing of International Patent Application No. PCT/EP2018/076066, filed Sep. 26, 2018, which claims priority to European Patent Application No. 17193218.9, filed Sep. 26, 2017, the entire disclosures of which are hereby incorporated herein by reference.

TECHNICAL FIELD OF THE INVENTION

The present invention relates to the field of surface chemistry, and more specifically to the manufacturing of shaped polymers of a surface-active macromolecule. The invention provides a method for manufacturing shaped polymers of a surface-active macromolecule, such as a silk protein.

BACKGROUND TO THE INVENTION

Humans have used silk produced by silkworms for a magnitude of applications for centuries. In recent years spider silk has received increased attention, mainly due to its superior mechanical strength (comparable to Kevlar), high elasticity, and, like silkworm silk, biocompatibility. As farming spiders is impractical due to the spiders' predatory nature, spider silk production became viable only after recombinant systems producing silk-mimicking proteins were made available. Using recombinant systems over natural harvesting is not only advantageous in terms of yield and reproducibility, but also because it allows functionalizing the silk, i.e. covalently linking a bioactive domain to the silk part.

Independent of whether the silk proteins are produced using recombinant systems or harvested directly from silkworms, they have to be transformed from soluble proteins into solid silk. The natural process used by spiders is intricate and involves a number of steps where the spidroins are converted into silk threads using an elongational flow through a narrowing duct that increases sheer forces in combination with an exchange of ions, rehydration, and a lowering of the pH. Attempts have been made to imitate the spinning process using, for example, microfluidic systems, wet-spinning, and electrospinning. Many of these processes are quite complex to design and require harsh chemicals such as methanol to render the threads water insoluble after formation, which, for functionalized silk, would kill the bioactivity.

Whereas spiders and silkworms typically generate silk in the shape of threads (1D), spidroins harvested from silkworms or produced recombinantly allow for generation of other shapes such as films (2D), particles/micro-spheres (3D), foams (3D), and gels (3D). Many of the methods for producing these shapes require the application of harsh chemicals.

Tsioris et al., Mater. Res. Soc. Proc. 1052: 1-7 (2007) describes a method for forming silk structures using a molded PDMS surface, wherein hydrophilicity and hydrophobicity is controlled. A silk solution is evenly deposited onto the surface and penetrates into hydrophilic channels of the pattern, where it is molded. The geometry and size of the formed silk structures depends on the mold of the PDMS. A challenge with the technique is to produce silk structures with any desired size, e.g. due to limitations in decasting of the formed structures from the PDMS mold. Tsioris et al. concludes that a critical part to success is the filling of the channel features without having liquid on the top surface of the PDMS stamp.

WO 2017/025964 describes fabrication of synthetic dragline spider silk. A fiber is described as a fine cord of fibrous material composed of two or more filaments twisted together. Hence, the structure is of considerable complexity as it comprises several filaments arranged in a complicated manner. WO 2017/025964 further speculates in different sizes of these filaments making up the fiber, but is completely silent about how to control this size.

Xu et al., Polymer 55(7):1845-1853 (2014) shows spider silk films casted onto glass slides using a double air interface. The size of the films generated by Xu et al can only be controlled by the size of a washer mounted on a slide, which is limiting.

Gomes et al., Biomaterials 32: 4255-4266 (2011) describes a method for expanding the function of spider silk proteins by fusing them to antimicrobial peptides.

Despite advances in the field, there is still a need for methods for manufacturing defined and reproducible microstructures of surface-active macromolecules, such as silk proteins.

SUMMARY OF THE INVENTION

It is an object of the present invention to provide a method for manufacturing defined and reproducible microstructures of surface-active macromolecules, such as silk proteins.

For these and other objects that will be evident from the following disclosure, the present invention provides according to a first aspect a method for manufacturing shaped polymers of surface-active macromolecules according to the appended claims and the itemized embodiments and as presented herein.

The manufacturing method is advantageous as it allows for manufacture of well-defined shapes and sizes of microstructures of e.g. silk proteins, which has not been possible with prior art methods.

The manufacturing method is particularly advantageous in providing reproducibility and control over the shapes and sizes of the microstructures.

The present invention further provides according to a second aspect spider silk structures according to the appended claims and the itemized embodiments and as presented herein.

The present invention further provides according to a third aspect a structure having a surface adapted to receive a droplet of an aqueous solution of surface-active macromolecules according to the appended claims and the itemized embodiments and as presented herein.

BRIEF DESCRIPTION OF THE DRAWINGS

FIGS. 1A-1C are a scheme of representative preparation methods and results.

FIGS. 3A-3H show results of Z-silk nanowire formation using the lateral droplet movement method.

LIST OF APPENDED SEQUENCES

Figure 2B:
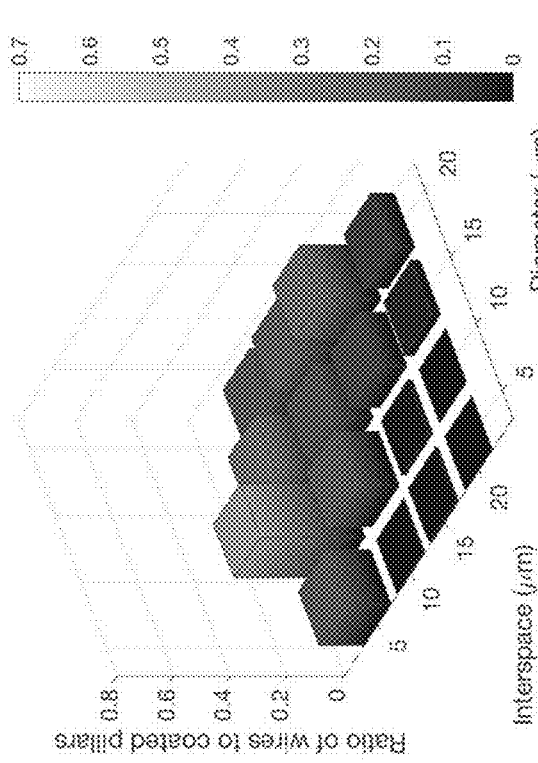
FIGS. 2A-2E show a characterization of localized Z-silk coatings generated using the touch-and-release method.

| SEQ ID NO: | |
|---|---|
| 1 | non-functionalized spider silk ("4RepCT") |
| 2 | Z-functionalized spider silk ("Z-4RepCT") |
| 3 | $FN_{cc}$-functionalized spider silk ("$FN_{cc}$-4RepCT") |
| 4 | CT |
| 5 | CT *Araneaus ventricosus* MiSp |
| 6 | IKVAV |
| 7 | YIGSR |
| 8 | EPDIM |
| 9 | NKDIL |
| 10 | GRKRK |
| 11 | KYGAASIKVAVSADR |
| 12 | NGEPRGDTYRAY |
| 13 | PQVTRGDVFTM |
| 14 | AVTGRGDSPASS |
| 15 | TGRGDSPA |
| 16 | CTGRGDSPAC |
| 17 | $FN_{cc}$ motif |

DETAILED DESCRIPTION OF THE INVENTION

The present invention is based on the insight that various silk formations can be generated by the interaction between soluble silk proteins and hydrophobic micropatterned surfaces. A hydrophobic micropatterned surface is a hydrophobic surface which is geometrically patterned. Structuring of a functionalized silk protein is achieved using micropatterned hydrophobic surfaces under conditions that retain the bioactivity of the functionalized silk. The retention of bioactivity is advantageous in numerous applications and is possible since no harsh chemicals and/or conditions are involved in the method. In the method presented herein to generate patterned silk sheets using microstructures, the liquid does not penetrate the pattern.

By combining hydrophobic and pattern surface characteristics with silk solution handling parameters, the present invention allows for controlled and reproducible generation of various shapes, including coatings, nanowires and sheets. A well-defined coating is obtained by temporary vertical deposition of a silk protein solution droplet onto protruding elements of the surface and removal of the droplet. Nanowires are obtained by lateral rolling of a droplet of silk proteins on a surface. Coherent sheets are obtained by vertical deposition of a droplet of silk solution onto a surface followed by evaporation. The structuring is obtained due to ordering of the surface active silk proteins at controlled interfaces. The silk formed in our work is in contact with a hydrophobic interface (including air) at all sides. Thus, this method should be applicable for any surface-active macromolecule that allows assembly into multimers or polymers.

A surface-active macromolecule is a macromolecule that is able to orient itself so as to expose hydrophilic regions into a polar environment and hydrophobic segments into an apolar phase. By doing so, the interfacial tension will be reduced. There are both natural and synthetic surface active polymers. The backbone can be either hydrophilic or hydrophobic, with side chains of the other property attached. Alternatively, the two properties (hydrophobic and hydrophilic) can be alternated in segments. Proteins can obtain surface activity either by having a protein chain with amino acids of alternated properties, or contain post translational modifications such as phosphate groups or carbohydrate residues that add specific features. Non-limiting examples of surface-active macromolecules include silk proteins (from spider or silkworm), milk proteins, muscle proteins (myosin), hydrophobins, globulin from black gram, rodlins, chaplins, polyanionic lipopolysaccharides, chitosan derivatives, and starch derivatives.

According to a first aspect of the invention, a method for manufacturing shaped polymers of surface-active macromolecules is comprising the steps of:

a) depositing an aqueous solution of the surface-active macromolecules on a surface; and b) forming shaped polymers of the surface-active macromolecules on the surface; and optionally c) removing the shaped polymers of the surface-active macromolecule from the surface.

In the method, the aqueous solution of the surface-active macromolecules is deposited in the form of a droplet. Furthermore, the surface is a hydrophobic micropatterned surface adapted to prevent the aqueous solution from penetrating into the pattern and to receive the droplet of the aqueous solution of the surface-active macromolecules and retain its droplet state. Preferably, the hydrophobic micropatterned surface is a superhydrophobic micropatterned surface having a contact angle of water of 90° or larger.

In a preferred embodiment, wherein surface-active macromolecules are proteins. In particular, the surface-active macromolecules may be silk proteins.

In certain preferred embodiments of the present invention, the silk protein is a fibroin. Fibroin is present in silk created by spiders, moths, such as silkworms, and other insects. Preferred fibroins are derived from the genus *Bombyx*, and preferably from the silkworm of *Bombyx mori*.

In certain preferred embodiments of the present invention, the silk protein is a spider silk protein. The terms "spidroins" and "spider silk proteins" are used interchangeably throughout the description and encompass all known spider silk proteins, including major ampullate spider silk proteins which typically are abbreviated "MaSp", or "ADF" in the case of Araneus diadematus. These major ampullate spider silk proteins are generally of two types, 1 and 2. These terms furthermore include non-natural proteins with a high degree of identity and/or similarity to the known spider silk proteins.

In some preferred embodiments of these and other aspects of the invention, the spider silk protein is comprising, or consisting of, the protein moieties REP and CT, wherein REP is a repetitive fragment of from 70 to 300 amino acid residues, selected from the group consisting of $L(AG)_nL$, $L(AG)_nAL$, $L(GA)_nL$, and $L(GA)_nGL$, wherein n is an integer from 2 to 10; each individual A segment is an amino acid sequence of from 8 to 18 amino acid residues, wherein from 0 to 3 of the amino acid residues are not Ala, and the remaining amino acid residues are Ala; each individual G segment is an amino acid sequence of from 12 to 30 amino acid residues, wherein at least 40% of the amino acid residues are Gly; and each individual L segment is a linker amino acid sequence of from 0 to 30 amino acid residues; and CT is a fragment of from 70 to 120 amino acid residues, having at least 70% identity to either of SEQ ID NO: 4-5. Optionally, a functional moiety is arranged either terminally in the spider silk protein, or between the moieties, or within any of the moieties, preferably terminally in the spider silk protein.

The spider silk protein typically comprises from 140 to 2000 amino acid residues, such as from 140 to 1000 amino acid residues, such as from 140 to 600 amino acid residues, preferably from 140 to 500 amino acid residues, such as from 140 to 400 amino acid residues. The small size is advantageous because longer proteins containing spider silk protein fragments may form amorphous aggregates, which require use of harsh solvents for solubilisation and polymerisation.

The spider silk protein may contain one or more linker peptides, or L segments. The linker peptide(s) may be arranged between any moieties of the spider silk protein, e.g. between the REP and CT moieties, at either terminal end of the spider silk protein or between the spidroin fragment and the cell-binding motif. The linker(s) may provide a spacer between the functional units of the spider silk protein, but may also constitute a handle for identification and purification of the spider silk protein, e.g. a His and/or a Trx tag. If the spider silk protein contains two or more linker peptides for identification and purification of the spider silk protein, it is preferred that they are separated by a spacer sequence, e.g. $His_6$-spacer-$His_6$-. The linker may also constitute a signal peptide, such as a signal recognition particle, which directs the spider silk protein to the membrane and/or causes secretion of the spider silk protein from the host cell into the surrounding medium. The spider silk protein may also include a cleavage site in its amino acid sequence, which allows for cleavage and removal of the linker(s) and/or other relevant moieties. Various cleavage sites are known to the person skilled in the art, e.g. cleavage sites for chemical agents, such as CNBr after Met residues and hydroxylamine between Asn-Gly residues, cleavage sites for proteases, such as thrombin or protease 3C, and self-splicing sequences, such as intein self-splicing sequences.

The protein moiety REP is fragment with a repetitive character, alternating between alanine-rich stretches and glycine-rich stretches. The REP fragment generally contains more than 70, such as more than 140, and less than 300, preferably less than 240, such as less than 200, amino acid residues, and can itself be divided into several L (linker) segments, A (alanine-rich) segments and G (glycine-rich) segments, as will be explained in more detail below. Typically, said linker segments, which are optional, are located at the REP fragment terminals, while the remaining segments are in turn alanine-rich and glycine-rich. Thus, the REP fragment can generally have either of the following structures, wherein n is an integer:

$L(AG)_nL$, such as $LA_1G_1A_2G_2A_3G_3A_4G_4A_5G_5L$;
$L(AG)_nAL$, such as $LA_1G_1A_2G_2A_3G_3A_4G_4A_5G_5A_6L$;
$L(GA)_nL$, such as $LG_1A_1G_2A_2G_3A_3G_4A_4G_5A_5L$; or
$L(GA)_nGL$, such as $LG_1A_1G_2A_2G_3A_3G_4A_4G_5A_5G_6L$.

It follows that it is not critical whether an alanine-rich or a glycine-rich segment is adjacent to the N-terminal or C-terminal linker segments. It is preferred that n is an integer from 2 to 10, preferably from 2 to 8, also preferably from 4 to 8, more preferred from 4 to 6, i.e. n=4, n=5 or n=6.

In some embodiments, the alanine content of the REP fragment is above 20%, preferably above 25%, more preferably above 30%, and below 50%, preferably below 40%, more preferably below 35%. It is contemplated that a higher alanine content provides a stiffer and/or stronger and/or less extendible fiber.

In certain embodiments, the REP fragment is void of proline residues, i.e. there are no Pro residues in the REP fragment.

Turning now to the segments that constitute the REP fragment, it is emphasized that each segment is individual, i.e. any two A segments, any two G segments or any two L segments of a specific REP fragment may be identical or may not be identical. Thus, it is not a general feature of the spidroin that each type of segment is identical within a specific REP fragment. Rather, the following disclosure provides the skilled person with guidelines how to design individual segments and gather them into a REP fragment, which is a part of a functional spider silk protein useful in a cell scaffold material.

Each individual A segment is an amino acid sequence having from 8 to 18 amino acid residues. It is preferred that each individual A segment contains from 13 to 15 amino acid residues. It is also possible that a majority, or more than two, of the A segments contain from 13 to 15 amino acid residues, and that a minority, such as one or two, of the A segments contain from 8 to 18 amino acid residues, such as 8-12 or 16-18 amino acid residues. A vast majority of these amino acid residues are alanine residues. More specifically, from 0 to 3 of the amino acid residues are not alanine residues, and the remaining amino acid residues are alanine residues. Thus, all amino acid residues in each individual A segment are alanine residues, with no exception or with the exception of one, two or three amino acid residues, which can be any amino acid. It is preferred that the alanine-replacing amino acid(s) is (are) natural amino acids, preferably individually selected from the group of serine, glutamic acid, cysteine and glycine, more preferably serine. Of course, it is possible that one or more of the A segments are all-alanine segments, while the remaining A segments contain 1-3 non-alanine residues, such as serine, glutamic acid, cysteine or glycine.

In an embodiment, each A segment contains 13-15 amino acid residues, including 10-15 alanine residues and 0-3 non-alanine residues as described above. In a more preferred embodiment, each A segment contains 13-15 amino acid residues, including 12-15 alanine residues and 0-1 non-alanine residues as described above. Without wishing to be bound by any particular theory, it is envisaged that A segments according to the invention form helical structures or beta sheets.

Furthermore, it has been concluded from experimental data that each individual G segment is an amino acid sequence of from 12 to 30 amino acid residues. It is preferred that each individual G segment consists of from 14 to 23 amino acid residues. At least 40% of the amino acid residues of each G segment are glycine residues. Typically, the glycine content of each individual G segment is in the range of 40-60%.

In certain embodiments, the first two amino acid residues of each G segment are not -Gln-Gln-.

Each individual L segment represents an optional linker amino acid sequence, which may contain from 0 to 30 amino acid residues, such as from 0 to 20 amino acid residues. While this segment is optional and not critical for the function of the spider silk protein, its presence still allows for fully functional spider silk proteins and polymers thereof which form fibers, films, foams and other structures. In particular, the amino acid sequence of a linker segment may resemble any of the described A or G segments, but usually not sufficiently to meet their criteria as defined herein.

In one embodiment of the REP fragment, one of the L segments contains 0 amino acids, i.e. one of the L segments is void. In another embodiment of the REP fragment, both L segments contain 0 amino acids, i.e. both L segments are void. Thus, these embodiments of the REP fragments according to the invention may be schematically represented as follows: $(AG)_nL$, $(AG)_nAL$, $(GA)_nL$, $(GA)_nGL$; $L(AG)_n$, $L(AG)_nA$, $L(GA)_n$, $L(GA)_nG$; and $(AG)_n$, $(AG)_nA$, $(GA)_n$, $(GA)_nG$. Any of these REP fragments are suitable for use with any CT fragment as defined below.

The CT fragment of the spidroin in the cell scaffold material has a high degree of similarity to the C-terminal amino acid sequence of spider silk proteins. As shown in WO 2007/078239, this amino acid sequence is well conserved among various species and spider silk proteins, including MaSp1, MaSp2 and MiSp (minor ampullate spidroin).

It is not critical which specific CT fragment is present in the spider silk protein in the cell scaffold material. A representative CT fragment is the amino acid residues 166-263 of SEQ ID NO: 1 derived from *Euprosthenops australis*, i.e. SEQ ID NO. 4. Another representative CT fragment is the MiSp sequence SEQ ID NO: 5. Thus, in one embodiment, the CT fragment has at least 70%, such as at least 80%, such as at least 85%, preferably at least 90%, such as at least 95%, identity to SEQ ID NO: 4 or SEQ ID NO: 5. The CT fragment may be identical to SEQ ID NO: 4 or SEQ ID NO: 5

The CT fragment typically consists of from 70 to 120 amino acid residues. It is preferred that the CT fragment contains at least 70, or more than 80, preferably more than 90, amino acid residues. It is also preferred that the CT fragment contains at most 120, or less than 110 amino acid residues. A typical CT fragment contains approximately 100 amino acid residues.

The term "% identity", as used herein, is calculated as follows. The query sequence is aligned to the target sequence using the CLUSTAL W algorithm (Thompson et al, Nucleic Acids Research, 22:4673-4680 (1994)). A comparison is made over the window corresponding to the shortest of the aligned sequences. The amino acid residues at each position are compared, and the percentage of positions in the query sequence that have identical correspondences in the target sequence is reported as % identity.

The term "% similarity", as used herein, is calculated as described above for "% identity", with the exception that the hydrophobic residues Ala, Val, Phe, Pro, Leu, Ile, Trp, Met and Cys are similar; the basic residues Lys, Arg and His are similar; the acidic residues Glu and Asp are similar; and the hydrophilic, uncharged residues Gln, Asn, Ser, Thr and Tyr are similar. The remaining natural amino acid Gly is not similar to any other amino acid in this context.

Throughout this description, alternative embodiments according to the invention fulfill, instead of the specified percentage of identity, the corresponding percentage of similarity. Other alternative embodiments fulfill the specified percentage of identity as well as another, higher percentage of similarity, selected from the group of preferred percentages of identity for each sequence. For example, a sequence may be 70% similar to another sequence; or it may be 70% identical to another sequence; or it may be 70% identical and 90% similar to another sequence.

In a preferred spider silk protein according to the invention, the REP-CT fragment has at least 70%, such as at least 80%, such as at least 85%, preferably at least 90%, such as at least 95% or even 100% identity to SEQ ID NO: 1.

The silk proteins are advantageously further containing a functional moiety. This functional moiety may be protein moiety as exemplified herein or a non-protein moiety. The functional moiety is arranged either terminally in the silk protein or within the silk protein, preferably N-terminally or C-terminally in the silk protein.

Desired bioactivities may be introduced by various bioactive proteins and peptides, such as a fibronectin peptide motif, which enhances cell adhesion and proliferation on the silk coatings, and the antimicrobial peptide Magainin I. The potential to include functional moieties is crucial in biomaterial applications in order to optimize the acceptance of the implants in the body and to tackle infection issues, which are also challenging successful implantation. Furthermore, more advanced bioactivities can be introduced using silk proteins fused to functional moieties in the form of protein domains with fold-dependent functions, such as affinity domains (e.g. Z domain binding IgG), enzymes (e.g. xylanase) or growth factors (e.g. fibroblast growth factor, FGF).

The spidroin fragment and the functional moiety are linked directly or indirectly to one another. A direct linkage implies a direct covalent binding between the moieties without intervening sequences, such as linkers. An indirect linkage also implies that the moieties are linked by covalent bonds, but that there are intervening sequences, such as linkers and/or one or more further moieties, e.g. 1-2 NT moieties.

The functional moiety may be arranged internally or at either end of the spider silk protein, i.e. C-terminally arranged or N-terminally arranged. It is preferred that the functional moiety is arranged at the N-terminal end of the spider silk protein. If the spider silk protein contains one or more linker peptide(s) for identification and purification of the spider silk protein, e.g. a His or Trx tag(s), it is preferred that it is arranged at the N-terminal end of the spider silk protein.

A preferred spider silk protein has the form of an N-terminally arranged functional moiety, coupled by a linker peptide of 0-30 amino acid residues, such as 0-10 amino acid residues, to a REP moiety. Optionally, the spider silk protein has an N-terminal or C-terminal linker peptide, which may contain a purification tag, such as a His tag, and a cleavage site.

The silk protein optionally contains a cell-binding motif (CBM) as a functional moiety. The optional cell-binding motif is arranged either terminally in the silk protein or within the silk protein, preferably N-terminally or C-terminally in the silk protein.

In certain preferred embodiments of these and other aspects of the invention, the functional moiety is a cell-binding motif selected from RGD, IKVAV (SEQ ID NO: 6), YIGSR (SEQ ID NO: 7), EPDIM (SEQ ID NO: 8), NKDIL (SEQ ID NO: 9), GRKRK (SEQ ID NO: 10), KYGAASIK-VAVSADR (SEQ ID NO: 11), NGEPRGDTYRAY (SEQ ID NO: 12), PQVTRGDVFTM (SEQ ID NO: 13), AVTGRGD-SPASS (SEQ ID NO: 14), TGRGDSPA (SEQ ID NO: 15), CTGRGDSPAC (SEQ ID NO: 16) and $FN_{cc}$ (SEQ ID NO: 17); and preferably from $FN_{cc}$, GRKRK, IKVAV, RGD and CTGRGDSPAC, more preferably $FN_{cc}$ and CTGRGD-SPAC; wherein $FN_{cc}$ is $C^1X^1X^2RGDX^3X^4X^5C^2$, wherein each of $X^1$, $X^2$, $X^3$, $X^4$ and $X^5$ are independently selected from natural amino acid residues other than cysteine; and $C^1$ and $C^2$ are connected via a disulphide bond.

In its most general form, $FN_{cc}$ is $C^1X^1X^2RGDX^3X^4X^5C^2$ (SEQ ID NO: 17); wherein each of $X^1$, $X^2$, $X^3$, $X^4$ and $X^5$ are independently selected from natural amino acid residues other than cysteine; and $C^1$ and $C^2$ are connected via a disulphide bond. $FN_{cc}$ is a modified cell-binding motif that imitates the α5β1-specific RGD loop motif of fibronectin by positioning cysteines in precise positions adjacent to the RGD sequence to allow formation of a disulphide-bridge to constrain the chain into a similar type of turn loop. This cyclic RGD cell-binding motif increases the cell adhesion efficacy to a matrix made of a protein containing the cell-binding motif, such as a recombinantly produced spider silk protein. The term "cyclic" as used herein refers to a peptide wherein two amino acid residues are covalently bonded via their side chains, more specifically through a disulfide bond between two cysteine residues. The cyclic RGD cell-binding motif $FN_{cc}$ promotes both proliferation of and migration by primary cells. Human primary cells cultured on a cell scaffold material containing the cyclic RGD cell-binding motif show increased attachment, spreading, stress fiber formation and focal adhesions compared to the same material containing a linear RGD peptide.

In preferred embodiments of $FN_{cc}$, each of $X^1$, $X^2$, $X^3$, $X^4$ and $X^5$ are independently selected from the group of amino acid residues consisting of: G, A, V, S, T, D, E, M, P, N and Q. In other preferred embodiments of $FN_{cc}$, each of $X^1$ and $X^3$ are independently selected from the group of amino acid residues consisting of: G, S, T, M, N and Q; and each of $X^2$, $X^4$ and $X^5$ are independently selected from the group of amino acid residues consisting of: G, A, V, S, T, P, N and Q. In certain preferred embodiments of $FN_{cc}$, $X^1$ is selected from the group of amino acid residues consisting of: G, S, T, N and Q; $X^3$ is selected from the group of amino acid residues consisting of: S, T and Q; and each of $X^2$, $X^4$ and $X^5$ are independently selected from the group of amino acid residues consisting of: G, A, V, S, T, P and N. In some preferred embodiments of $FN_{cc}$, $X^1$ is S or T; $X^2$ is G, A or V; preferably G or A; more preferably G; $X^3$ is S or T; preferably S, $X^4$ is G, A, V or P; preferably G or P; more preferably P; and $X^5$ is G, A or V; preferably G or A; more preferably A.

In certain preferred embodiments of $FN_{cc}$, the cell-binding motif is comprising the amino acid sequence CTGRGD-SPAC (SEQ ID NO: 16). Further preferred cyclic RGD cell-binding motifs according to the invention display at least 60%, such as at least 70%, such as at least 80%, such as at least 90% identity to CTGRGDSPAC (SEQ ID NO: 16), with the proviso that position 1 and 10 are always 0; position 4 is always R; position 5 is always G; position 6 is always D; and positions 2-3 and 7-9 are never cysteine. It is understood that the non-identical positions among positions 2-3 and 7-9 can be freely selected as set out above.

A preferred group of cell-binding motifs are $FN_{cc}$, GRKRK, IKVAV, and RGD, and in particular $FN_{cc}$, such as CTGRGDSPAC.

In a preferred embodiment, the invention utilizes solutions of silk proteins on hydrophobic surfaces to generate three distinct formations of silk: localized coatings, arrays of localized directional wires, and free silk sheets, i.e. free-standing silk sheets. In one preferred embodiment, the silk formation is a free-standing nanowire. Free-standing implies that the structure is produced without being attached to any supporting structure. Free-standing structures can be removed without harsh treatments, e.g. heat, which substantially alters the secondary structure of the silk protein. Schematics of the preparation methods and representative results are shown in FIGS. 1A-1C:

FIG. 1A) perpendicular deposition and immediate removal of the silk solution droplet on protruding elements of the surface, resulting in localized silk coatings on the top of the protruding elements;

FIG. 1B) lateral rolling of the silk solution droplet on the protruding elements results in silk nanowire formation; and FIG. 1C) perpendicular attachment of the silk solution droplet to the protruding elements, followed by evaporation, resulting in the formation of a silk sheet.

The generation of these three formats using our facile and rapid method has several potential applications, both as is on the surface: localized microstructure coatings on protruding elements of the surface could find use as miniaturized microarrays, wires could be used as optical waveguides, and sheets could be used for cell-culture applications; and when released from the surface: released (i.e. free-standing) coatings and wires could be used as suspended vehicles for biomedical applications and the cell growth applications for the sheets could be extended by pre-patterning with different antibodies before sheet generation and thereby steering the cell growth.

Beyond presenting the three exemplary techniques and their corresponding silk formations, we also investigate growth parameters for each formation. By placing silk protein solution droplets in the Cassie-Baxter state on super-hydrophobic surfaces, we promote silk-silk interaction at the liquid:solid and liquid:air interface. Thereby it is possible to generate formations of functionalized silk under mild conditions, resulting in silk structures with retained bioactivity. Herein we demonstrate this principle for two differently functionalized silk proteins; Z-silk which has selective affinity for antibodies making it suitable for diagnostic applications, and $FN_{cc}$-silk which harbors cell binding ability and thereby is useful for cell culture applications.

In a preferred embodiment, the hydrophobic micropatterned surface is a superhydrophobic micropatterned surface having a contact angle of water of 90° or larger, such as 100° or larger, such as 120° or larger, or even 150° or larger, as measured by drop shape analysis. A superhydrophobic micropatterned surface is a superhydrophobic surface which is geometrically patterned. A superhydrophobic surface is a surface that is non-wetting due to its surface structure. Water cannot penetrate into such structures, so the silk protein assembles at the three-point interface between the hydrophobic surface, the liquid and surrounding air. A liquid on contact with the surface will typically feature a contact angle above 90°, such as above 100°. There are several examples of such surfaces in nature, the most well-known being the self-cleaning lotus-leaf.

The superhydrophobic patterns advantageously produce individual nanofibrils and nanowires of controlled sizes. The nanofibrils and nanowires can be produced as free-standing nanofibrils and nanowires. Similarly, the three-point interface between the superhydrophobic surface, the liquid and air allow the silk to assemble into thin sheets, which are removable. The sheets can thus be produced as free-standing sheets.

In one preferred embodiment, the hydrophobic micropatterned surface includes protruding elements interspaced by a distance i of 1-100 μm, and wherein the protruding elements have a largest lateral extension d of 1-100 μm. Preferably, the protruding elements have a largest lateral extension d of 1-50 μm, such as 5-30 μm. Preferably, the interspace distance i between the protruding elements is 1-50 μm, such as 5-30 μm.

In a preferred embodiment, the protruding elements are pillar-shaped, and wherein the largest lateral extension d is the largest diameter of the pillar. Pillar surfaces can be prepared in many ways for example using layer-by-layer and colloidal assembly, self-assembly, natural folding, and lithography and etching. Depending on how the process is done different types of pillar structures can be achieved, for example: "I" shaped pillars which are straight rods, "T" shaped pillars which are called single reentrant structures, and times new roman "T" shaped pillars which are called double reentrant structures. The first two of these needs to be coated with a hydrophobic material (for example $C_4F_8$) to become superhydrophobic while the last can be made from a hydrophilic material (for example $SiO_2$).

A wide range of materials can be used to manufacture superhydrophobic surface ranging from hydrophobic materials for example, but not limited to, fluorinated polymers (Teflon), silicones (PDMS), organic materials (polyethylene, polyamide, polycarbonate), and inorganic materials (ZnO, $TiO_2$). However, by structuring the pillars correctly it is also possible to make superhydrophobic surfaces using hydrophilic materials such as $SiO_2$.

In certain embodiments, the hydrophobic micropatterned surface comprises silicon. In one preferred embodiment, the hydrophobic micropatterned surface is made of silicon.

In some embodiments, the hydrophobic micropatterned surface comprises an outer layer of a hydrophobic coating material, such as a perfluorocarbon compound.

In certain embodiments, the hydrophobic micropatterned surface comprises an outer layer of a superhydrophobic coating material.

According to a second aspect, the present invention provides novel silk structures, preferably spider silk structures:

(i) A coating having a lateral extension of 1-100 μm attached to a protruding element of a hydrophobic micropatterned surface. Preferably, the hydrophobic micropatterned surface is a superhydrophobic micropatterned surface having a contact angle of water of 90° or larger. Preferably, the coating has a lateral extension of 5-30 μm, such as 5-20 μm.

(ii) A nanowire having a length of 1-100 μm and a thickness of 10-372.5 nm, such as 10-300 nm, 10-200 nm, preferably 10-100 nm. Preferably, the nanowire has a length of 5-30 μm, such as 5-20 μm, and/or a thickness of 36-88 nm. Preferably, the nanowires are free-standing. For avoidance of doubt, a nanowire is a single filament of ordered proteins, e.g. silk proteins.

(iii) A silk sheet having a thickness of 1-10 μm. Preferably, the silk sheet has a thickness of 2-8 μm, such as 3-5 μm. Preferably, the silk sheets are free-standing.

According to a third aspect, the present invention provides a structure having a surface adapted to receive a droplet of an aqueous solution of surface-active macromolecules, such as silk proteins, wherein the surface is hydrophobic and comprises a pattern of microstructures; wherein the surface is adapted to prevent the aqueous solution from penetrating into the pattern and to retain its droplet state; and wherein the surface is adapted to allow formation of shaped polymers of the surface-active macromolecules thereto. Preferably, the hydrophobic surface is a superhydrophobic surface having a contact angle of water of 90° or larger.

Preferred features of this structure and its surface are evident from the detailed description hereinabove. The structure is useful for the manufacture of a shaped polymer made of surface-active macromolecules as set out hereinabove.

ITEMIZED LISTING OF EMBODIMENTS

1. A method for manufacturing shaped polymers of surface-active macromolecules, comprising the steps of:

a) depositing an aqueous solution of the surface-active macromolecules on a surface, wherein the aqueous solution of the surface-active macromolecules is deposited in the form of a droplet, and wherein the surface is a hydrophobic micropatterned surface adapted to prevent the aqueous solution from penetrating into the pattern and to receive the droplet of the aqueous solution of the surface-active macromolecules and retain its droplet state; and b) forming shaped polymers of the surface-active macromolecules on the surface.

2. A method according to any previous embodiment, wherein the surface-active macromolecules are proteins.

3. A method according to embodiment 2, wherein the surface-active macromolecules are silk proteins, such as spider silk proteins.

4. A method according to embodiment 3, wherein the silk proteins are further containing a functional moiety.

5. A method according to any previous embodiment, wherein the depositing of step a) is achieved by a motion of the droplet towards the surface along a direction intersecting the plane of the surface.

6. A method according to embodiment 5, wherein the depositing of step a) is achieved by an essentially perpendicular motion of the droplet in relation to the plane of the surface.

7. A method according to any previous embodiment, wherein the forming of step b) comprises removing the deposited droplet from the surface by a motion of the droplet away from the surface along a direction intersecting the plane of the surface.

8. A method according to embodiment 7, wherein the deposited droplet is removed from the surface by an essentially perpendicular motion of the droplet in relation to the plane of the surface.

9. A method according to any one of embodiments 7-8, wherein the droplet is removed within 30-240 seconds, such as within approximately 60 seconds, after the depositing step a) has been completed.

10. A method according to any one of embodiments 7-9, wherein the forming of step b) does not comprise any lateral movement of the deposited droplet on the surface prior to its removal.

11. A method according to any one of embodiments 7-9, wherein the forming of step b) comprises moving the deposited droplet laterally on the surface prior to its removal.

12. A method according to embodiment 11, wherein the droplet moving speed (s) is in the range of $0.1\text{-}10$ mm $s^{-1}$, such as approximately 5 mm $s^{-1}$.

13. A method according to any one of embodiments 1-6, wherein the forming of step b) involves evaporating the deposited droplet on the surface.

14. A method according to any previous embodiment, wherein the hydrophobic micropatterned surface is a superhydrophobic micropatterned surface having a contact angle of water of 90° or larger.

15. A method according to any previous embodiment, wherein the hydrophobic micropatterned surface includes protruding elements interspaced by a distance i of 1-100 μm, and wherein the protruding elements have a largest lateral extension d of 1-100 μm.

16. A method according to embodiment 15, wherein the protruding elements have a largest lateral extension d of 1-50 μm, such as 5-30 μm.

17. A method according to any one of embodiments 15-16, wherein the interspace distance i between the protruding elements is 1-50 μm, such as 5-30 μm.

18. A method according to any one of embodiments 15-17, wherein the protruding elements are pillar-shaped, and wherein the largest lateral extension d is the largest diameter of the pillar.

19. A method according to any previous embodiment, wherein the hydrophobic micropatterned surface comprises silicon.

20. A method according to any previous embodiment, wherein the hydrophobic micropatterned surface comprises an outer layer of a hydrophobic coating material.

21. A method according to embodiment 20, wherein the hydrophobic coating material is a perfluorocarbon compound.

22. A method according to any previous embodiment, further comprising the step of:
   c) removing the shaped polymers of the surface-active macromolecule from the surface.

23. A method according to any previous embodiment, wherein the aqueous solution of the surface-active macromolecules is comprising a carbonate buffer.

24. A spider silk structure selected from the group consisting of
   (i) a coating having a lateral extension of 1-100 µm attached to a protruding element of a hydrophobic micropatterned surface;
   (ii) a nanowire having a length of 1-100 µm and a thickness of 10-100 nm; and
   (iii) a silk sheet having a thickness of 1-10 µm.

25. A spider silk structure according to embodiment 24, which is (i) a coating having a lateral extension of 5-30 µm, such as 5-20 µm, attached to a protruding element of a hydrophobic micropatterned surface.

26. A spider silk structure according to embodiment 24, which is (ii) a nanowire having a length of 5-30 µm, such as 5-20 µm, and/or a thickness of 36-88 nm.

27. A spider silk structure according to embodiment 24, which is (iii) a silk sheet having a thickness of 2-8 µm, such as 3-5 µm.

28. A structure having a surface adapted to receive a droplet of an aqueous solution of surface-active macromolecules, wherein the surface is hydrophobic and comprises a pattern of microstructures; wherein the surface is adapted to prevent the aqueous solution from penetrating into the pattern and to retain its droplet state; and wherein the surface is adapted to allow formation of shaped polymers of the surface-active macromolecules thereto.

29. A structure according to embodiment 28, wherein the hydrophobic surface is a superhydrophobic surface having a contact angle of water of 90° or larger, such as 120° or larger, such as 150° or larger.

30. A structure according to any one of embodiments 28-29, wherein the hydrophobic micropatterned surface includes protruding elements interspaced by a distance i of 1-100 µm, and wherein the protruding elements have a largest lateral extension d of 1-100 µm.

31. A structure according to embodiment 30, wherein the protruding elements have a largest lateral extension d of 1-50 µm, such as 5-30 µm.

32. A structure according to any one of embodiments 30-31, wherein the interspace distance i between the protruding elements is 1-50 µm, such as 5-30 µm.

33. A structure according to any one of embodiments 30-32, wherein the protruding elements are pillar-shaped, and wherein the largest lateral extension d is the largest diameter of the pillar.

34. A structure according to any one of embodiments 28-33, wherein the hydrophobic micropatterned surface comprises silicon.

35. A structure according to any one of embodiments 28-34, wherein the hydrophobic micropatterned surface comprises an outer layer of a hydrophobic coating material.

36. A structure according to embodiment 35, wherein the hydrophobic coating material is a perfluorocarbon compound.

37. A structure according to any one of embodiments 28-36, further comprising a shaped polymer of the surface-active macromolecules on the surface.

38. Use of a structure according to any one of embodiments 28-37 for the manufacture of a shaped polymer made of surface-active macromolecules.

EXAMPLES

Microarrays of protruding elements shaped as circular silicon pillars with varying diameter (d) and interspace (i), including where d,i=5, 10, 15, or 20 µm, were prepared using standard microfabrication processes and coated with a hydrophobic layer using plasma deposition.

Functionalized soluble silk proteins were prepared as described e.g. in Jansson et al., Biomacromolecules 15: 1696 (2014). A droplet of silk solution was then manipulated on the surface using one of three methods: touch-and-release, lateral droplet movement, or drop casting, as illustrated in FIGS. 1A-1C and detailed in the experimental section. The anti-wetting property of the surface prevents the liquid from penetrating the pillars, i.e. retaining the Cassie-Baxter state, and results in the three methods generating, respectively, localized coatings, nanowires, and sheets of silk. The bioactivity of the Z-silk was confirmed by successful staining using labeled antibodies, which was exploited for the visualization of the silk coatings and nanowire structures using fluorescence microscopy. Independently of how the droplets were manipulated, the top surfaces of the pillars in contact with the silk solution were always coated with silk. Furthermore, the formation of silk is surprisingly advantageous in that the silk proteins self-assemble into silk at all hydrophobic surfaces, i.e. both the lower liquid:protruding element interface and the upper liquid:air interface.

In a preferred embodiment, the depositing of method step a) is achieved by a motion of the droplet towards the surface along a direction intersecting the plane of the surface. Preferably, the depositing of method step a) is achieved by an essentially perpendicular motion of the droplet in relation to the plane of the surface.

In one preferred embodiment, the shape forming of method step b) comprises removing the deposited droplet from the surface by a motion of the droplet away from the surface along a direction intersecting the plane of the surface. Preferably, the deposited droplet is removed from the surface by an essentially perpendicular motion of the droplet in relation to the plane of the surface. It is preferred that the droplet is removed within 30-240 seconds, such as within approximately 60 seconds, after the depositing step a) has been completed.

In certain embodiments, the forming of method step b) does not comprise any lateral movement of the deposited droplet on the surface prior to its removal. This allows for the manufacture of localized surface coating on any protruding elements of the surface.

Figure 2E:
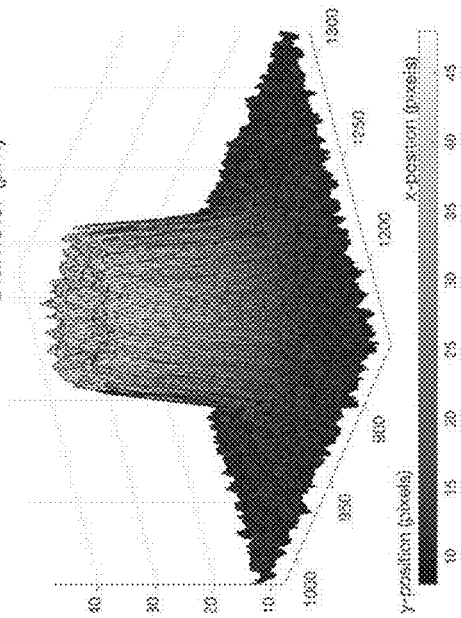
Figure 2A:
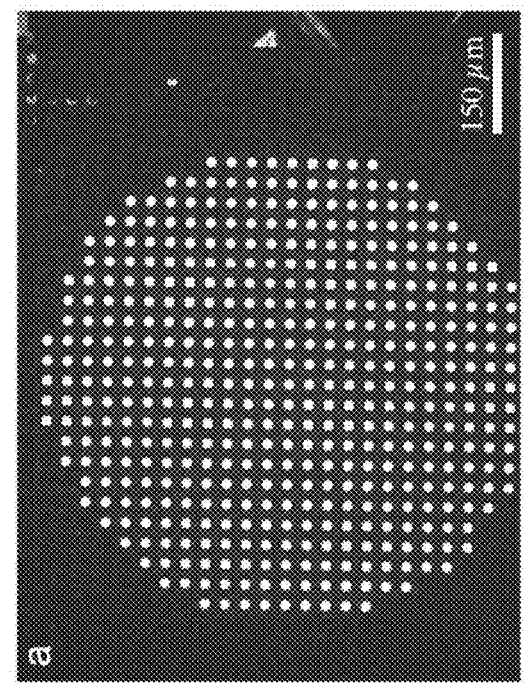

FIGS. 2A-2E show a characterization of localized Z-silk coatings generated using the touch-and-release method. FIG. 2A shows a fluorescence microscopy image of a Z-silk coated micropillar array (d=15 µm; i=15 µm). FIG. 2B) shows amount of silk wires generated in relation to the amount of coated pillars for surfaces with different pillar diameter and interspace, where zero wires would be typically desired for array coating applications. Uniform localized surface coatings without wires were formed using the touch-and-release method on surfaces with high pillar interspace (i≥15 µm) and low diameter (d≤10 µm) (FIG. 2B). When the silk solution was removed vertically from the surface, microdroplets were left behind on top of the pillars, which evaporated and resulted in a silk coating. Thus, silk proteins self-assemble into silk at all hydrophobic surfaces, i.e. both the liquid:pillar interface and the liquid:air interface.

To study the stability of the coating, surfaces with d=15 µm and i=20 µm were coated with silk, stained with IgG-Alexa Fluor 488 and then submersed in water for either 1, 2, 8, 24 or 48 hours. The samples were then re-stained with IgG-Alexa Fluor 488. Images were taken both before and after submersion. The silk coatings remained attached to the pillars when submersed in water for up to 8 hours. The water that the surfaces had been incubated in was dried on glass slides and fluorescence images of the dried solution revealed that the coatings had been released into solution in the form of mini-sheets. After 24 hours the majority of the coatings had been released in the form of mini-sheets into the water.

Figure 2D:
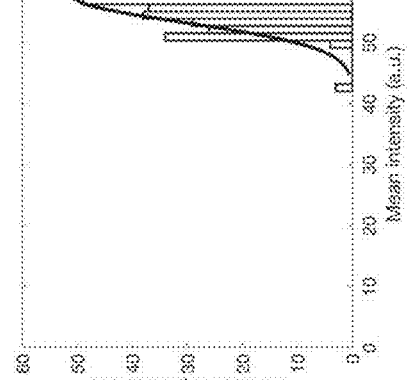
Figure 2C:
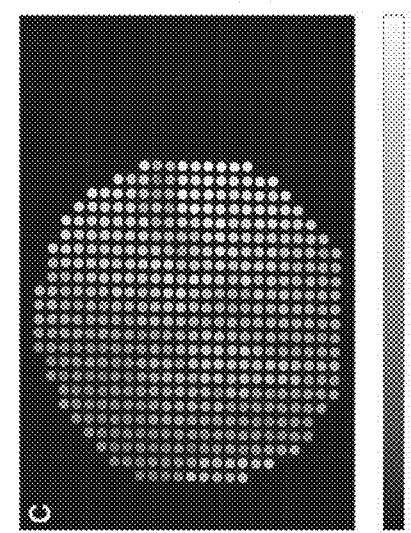

FIG. 2C) shows mean fluorescence intensity of FIG. 2A). FIG. 2D) shows a histogram of the mean intensity of each pillar in FIG. 2A) with a normal Gaussian fit with 9% standard variation. Silk-coated pillar arrays without wires or sheets featured relatively uniform coatings (FIG. 2C-2D). Comparing samples processed on pillar arrays with the same geometry, the array-to-array average fluorescence intensity distribution has an average standard deviation of 2.5% (min 0.3%; max 5.7%). The pillar-to-pillar average fluorescence intensity distribution within an array has an average standard deviation of 6.6% (min 2.1%; max 16.1%). We typically observed a slight intensity gradient across the coated array (FIG. 2C), which likely is caused by differences in contact time between the silk solution and the pillars due to uneven removal of the droplet. The fluorescence intensity distribution on the individual pillars had an average standard deviation of 9.8% (min 5.0%; max 20.3%). FIG. 2E) shows a surface profile of the fluorescence intensity of one pillar. We typically observed a higher intensity at the edge of the pillars compared to the center (FIG. 2E), which can be ascribed to the coffee ring effect. SEM and AFM images of the pillar surfaces do not reveal any surface roughness. The overhang geometry of the pillars prevents galvanically contacting the pillar top surfaces, which limits the magnification in SEM imaging due to charging of the coatings. The lack of detail in AFM images may be caused by the softness of the coatings. After the coatings have been released and dried under vacuum, they reveal a contracted, non-uniform surface. However, this geometry is not necessarily representative of the coatings when adhered to the pillars or other protruding elements.

In one embodiment, the forming of method step b) comprises moving the deposited droplet laterally on the surface prior to its removal. It is preferred that the droplet moving speed (s) is in the range of 0.1-10 mm s$^{-1}$, such as approximately 5 mm s$^{-1}$. This allows for the manufacture of extended shapes, such as nanowires.

FIGS. 3A-3H present results of Z-silk nanowire formation using lateral droplet movement on an array with pillar diameter d=15 µm and interspace i=10 µm with droplet speed of 10 mm s$^{-1}$. FIGS. 3A-3C show images of Z-silk nanowires generated using lateral droplet movement: 3A) top view fluorescent image after nanowire formation; 3B) magnification of 3A); 3C) SEM image of the pillars, their coatings in form of a wrinkled sheet, and the nanowires in between.

The diameter of the wires was studied for three different surface geometries, (d, i)=(15 µm, 5 µm), (20 µm, 5 µm) and (20 µm, 10 µm), and for droplet speeds, s, between 0.1 and 10 mm s$^{-1}$. Further in FIGS. 3A-3H, average amount of wires generated in relation to the amount of coated pillars for lateral droplet movement with speed 3d) 0.1 mm s$^{-1}$, 3E) 10 mm s$^{-1}$, 3f) for speeds 0.1-10 mm s$^{-1}$ for a surface with d=15 µm and i=5 µm; histograms of the average wire diameter with a normal Gaussian fit for 3G) (d, i, s)=(15 µm, 5 µm, 1 mm s$^{-1}$), i.e. the parameters resulting in the lowest relative wire diameter variability, and 3H) (d, i, s)=(15 µm, 5 µm, 5 mm s$^{-1}$), i.e. the parameters resulting in the largest wire yield. The largest average wire diameter measured was 372.5±85 nm for (d, i, s)=(15 µm, 5 µm, 0.1 mm s$^{-1}$) and the smallest was 168.9±36 nm for (d, i, s)=(20 µm, 5 µm, 0.1 mm s$^{-1}$). The wire diameters did not vary significantly for different droplet speeds. Also for geometries (d, i)=(15 µm, 5 µm) and (20 µm, 10 µm) there was no significant difference in wire diameter. However, the wire diameters generated for geometry (d, i)=(20 µm, 5 µm), the highest d:i ratio, were significantly smaller than those for the other two geometries. The absolute variation of the wire diameters on each sample varied between 36 and 88 nm, and no correlation was found between this variation and the surface geometry parameters d and i, or droplet speed, s. The variation in diameter was uniformly distributed throughout the droplet path and the directionality of the wires was found to be independent of the speed. This data points towards a high repeatability in the generation of wires in the same direction.

The formation of the spider silk nanowires on superhydrophobic surfaces is not only governed by surface energy minimization of the interfaces between a single liquid, gas, and solid phase. Spider silk wire formation is surprisingly additionally governed by the surface energy of a self-assembled second solid phase, the silk, at the liquid:gas and liquid:solid interfaces. It has been observed that wire formation starts at the receding droplet interface with the formation of what looks like a local veil between the pillars, followed by the contraction of that veil into a wire shape. We hypothesize that the formation of these structures starts with a self-assembled, but not yet solidified, silk layer at the top and bottom surface of the veil, with a thin liquid layer in-between. The liquid is removed from this veil by evaporation to the environment and/or by convective transport from the veil to the moving droplet. During this process, the sections of the veil on top of the pillars contract to a sheet, and the sections suspended between the pillars further contract to form wires. The contracted sheets on the pillars are visible in the fluorescence images as a distinct dark stripe in the center of the pillars (FIG. 3B), and their wrinkles can be clearly observed in the SEM images (FIG. 3C). The resulting average pillar-to-pillar fluorescence intensity standard deviation of 12.5% (min 3.8%; max 28.4%) is almost double that for surfaces where no wires were formed, confirming the difference in pillar coating formation. A weak correlation was found between the wire and pillar coating intensities.

The yield of the wires, here defined as the ratio of the amount of wires over the amount of coated pillars, was found to depend on three parameters (see FIGS. 3D-3F): (1) decreasing the pillar interspace generated more wires; (2) increasing the pillar diameter generated more wires; and (3)

the droplet moving speed, where s=5 mm s$^{-1}$ generated more wires more consistently than higher and lower droplet speeds. Self-assembly of the silk is expected to occur in preference under low flow velocity conditions at the liquid: air interface, and where water removal by evaporation locally increases the silk protein concentration. Low flow velocity is expected for low droplet speed, which would explain increased wire formation for d=5 μm at 0.1 mm s$^{-1}$ droplet speed compared to 10 mm s$^{-1}$. Apparent wall slip on superhydrophobic surfaces decreases with decreasing pillar interspace and increasing pillar diameter, resulting in a lower flow velocity at the bottom liquid:air interface. Indeed, more wires are formed on such geometries under all flow conditions. The veil has smaller dimensions than the droplet, thus high droplet speed leads to relatively larger flow resistance in the veil compared to that in the droplet, i.e. the liquid in the veil "cannot follow" the droplet. Water removal by evaporation will increase over convection under such conditions, which would explain increased wire formation on surfaces with large pillar diameter for 10 mm s$^{-1}$ droplet speed compared to 0.1 mm s$^{-1}$. The influence of the speed on the yield of wires was further studied for (d, i)=(15 μm, 5 μm) and the highest yield was found for a speed of 5 mm s$^{-1}$. Comparing this with the variation in diameter, which was the lowest for the same surface but a speed of 1 mm s$^{-1}$, there seems to be a trade-off between yield and uniformity.

The wires were found to remain on the surface after being submersed in water for 48 hours. It was, however, possible to release the wires from the substrate by sonicating the samples for 10 minutes. The wires were also successfully transferred from the superhydrophobic substrate to a flat off-stoichiometry thiol-ene polymer (OSTE) surface by contact printing.

In a preferred embodiment, the forming of step b) involves evaporating the deposited droplet on the surface. This implies that the forming of step b) involves evaporating the deposited droplet in its intact state on the surface. This allows for the manufacture of sheet structures.

Figure 4A:
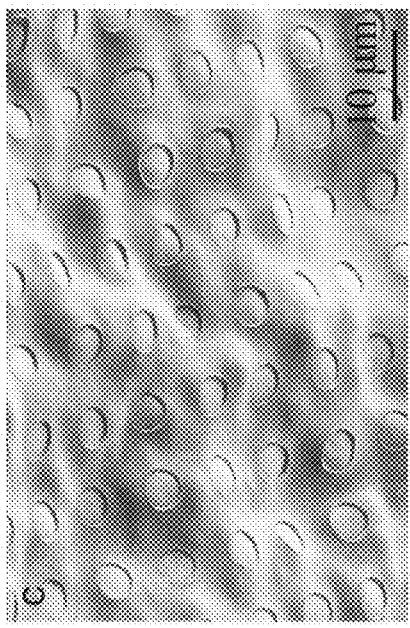
FIGS. 4A-4E show results of the drop casting silk sheet formation protocol.
Figure 4B:
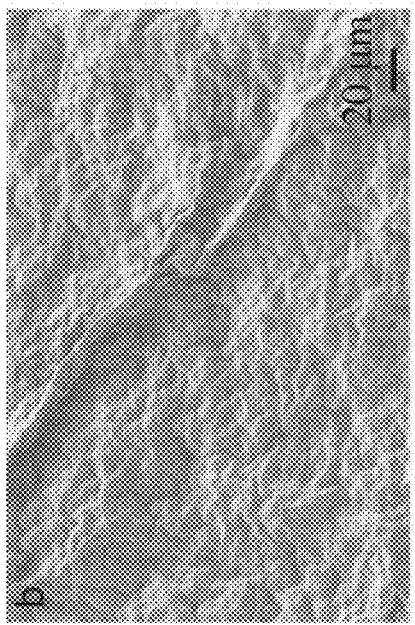
Figure 4C:
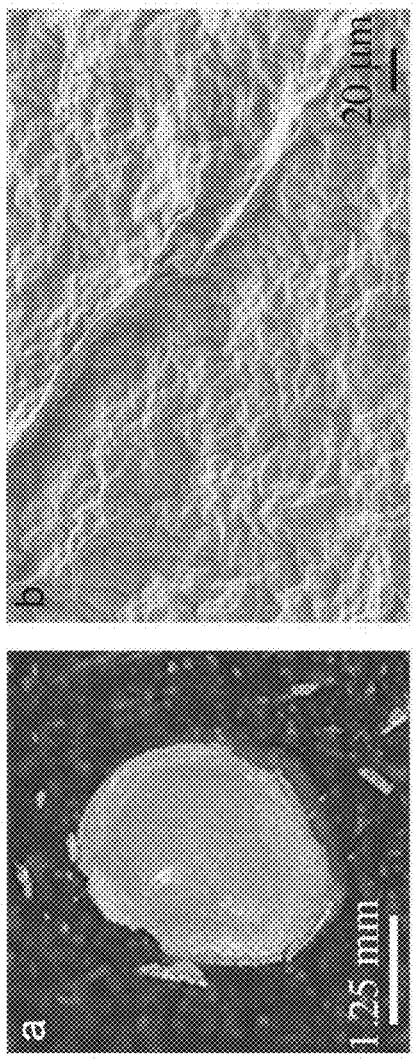
Figure 4D:
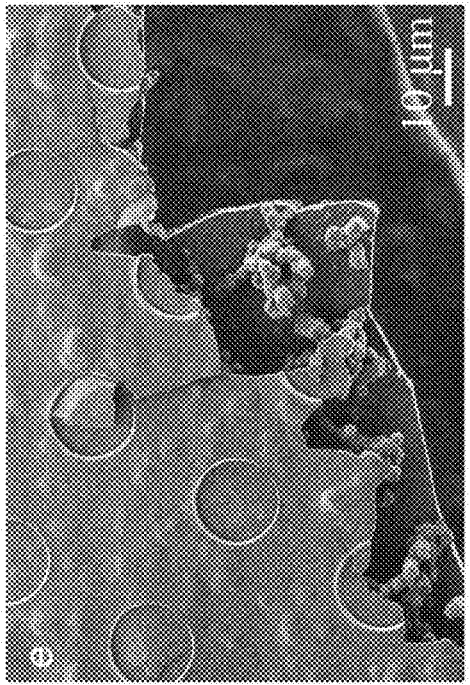
Figure 4E:
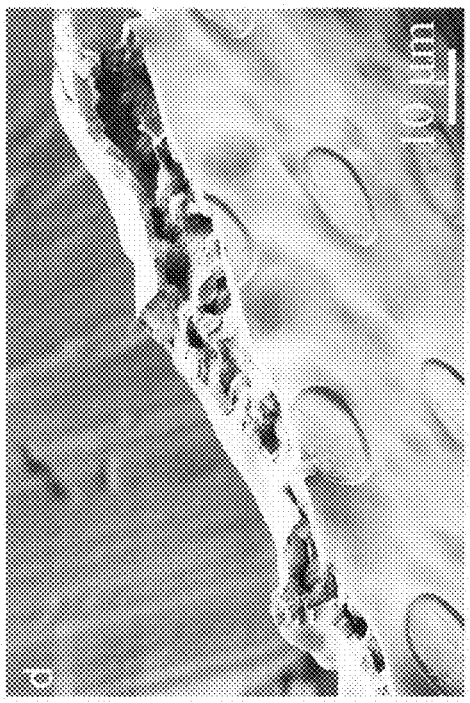

FIGS. 4A-4E present the results of the drop casting silk sheet formation protocol. FIG. 4A) is a photograph of a non-functionalized silk sheet (NH$_4$HCO$_3$ buffer, ambient conditions). SEM images of the FIG. 4B) top and FIG. 4C) bottom side of a FN$_{cc}$-silk sheet (NaHCO$_3$ buffer, ambient conditions) after release are shown. FIG. 4D) is SEM side view of a broken non-functionalized silk sheet showing the bottom and top layer and the internal structure (NH$_4$HCO$_3$ buffer, ambient conditions). FIG. 4E) is a SEM top view of a non-functionalized silk sheet showing the bottom and top layer and the internal structure (NH$_4$HCO$_3$ buffer, humid conditions).

Insoluble silk sheets were generated using drop casting and evaporation under mild conditions (FIG. 4A). In contrast to previous reports, no harsh post-treatments were needed to render the sheets water insoluble. We ascribe this to the increased hydrophobicity of our surfaces, which supports the transition of silk proteins from random/helical to beta-sheet formation and thus renders the sheets more stable. This is supported by SEM images showing that sheets consist of two layers of silk, one on the top and one on the bottom of the sheet, with aggregates of silk protein in-between (FIGS. 4D-4E). The sheet internal structure can also be seen using confocal microscopy. The top and bottom layers are formed during silk self-assembly at the hydrophobic air and pillar surfaces. The unordered silk structures in-between result from spontaneous aggregation of proteins that are trapped between the silk sheets during evaporation. From the SEM images it appears as though the surface profile of the sheets is generated from the aggregate silk structures between the top and bottom silk layers (FIG. 3E). This is further observed using confocal microscopy, where no variations above a few micrometers can be observed.

This type of sheet formation occurred for all tried combinations of surfaces, buffers, concentrations, and types of silk, albeit with some distinct differences. Sheets generated from high silk protein concentration solutions are less transparent (i.e. it is not possible to see the bottom substrate through the sheet) than those made from low concentration of silk protein. This is because they are thicker and contain a higher density of silk aggregates between the top and bottom silk layers. Sheets generated on structured substrates using a 0.3 mg ml$^{-1}$ spidroin concentration had a thickness around 1 μm while sheets generated using a 3 mg ml$^{-1}$ spidroin concentration had a thickness around 10 μm. Sheet generation under high humidity conditions resulted in a slightly larger average sheet size, and in an increased variation of sheet size compared to those for sheets generated at low humidity. Sheets generated on structured surfaces were smaller than those on unstructured surfaces, which can be expected from the reduced wettability.

Sheets generated on structured surfaces using 3 mg mL$^{-1}$ silk solution in carbonate buffers (NH$_4$HCO$_3$ or NaHCO$_3$) could typically be manually removed from the surface after drying. All other solutions generated sheets that were stuck on the surface in dry format. For buffers that resulted in sheets that were stuck when generated on the flat surface, but not the structured surface, we hypothesize that this is due to a reduced surface interaction on the structured surface. The increased sheet adhesion when using Tris buffer can be ascribed to the formation of salt crystals upon drying, which increases the interaction between the silk and the surface. The latter observation is supported by a previous study where volatile carbonate based buffers were used. Sheet that were stuck after drying could be released in wet format after typically 2 hours of submersion in water, except for non-functionalized silk sheets from NH$_4$HCO$_3$ buffer casted on flat surfaces, which remained stuck after 48 hours. Noteworthy is that the sheets generated using Tris buffer on structured surfaces and on flat surfaces had a tendency to split into two layers upon submersion, where the bottom layer remained adhered to the surface and the top layer could be lifted off. The stability of the sheets was tested by submerging them in water for 48 hours or in cell culture media for over 7 days. The sheets remained intact, without visual signs of being dissolved, confirming that the proteins had transformed into a stable silk form.

In summary, we have identified specific parameters for the formation of silk coatings, nanowires, and sheets on superhydrophobic surfaces:
i) touching and immediately perpendicularly removing the silk solution droplet on an array of protruding elements with small diameter and large interspace results in coatings without wires;
ii) moving the silk solution droplet laterally with appropriate speed along an array of protruding elements with large diameter and small interspace generates a large amount of aligned wires; and
iii) evaporating a droplet of a high concentration of silk protein on top of a array of protruding elements generates a silk sheet that can be released from the surface.

Experimental Section
Manufacturing of Surfaces:
Chips with arrays of reentrant silicon micropillars, with top diameters, d, and interspace, i, of 5, 10, 15, and 20 μm, and unpatterned surfaces were fabricated using standard microfabrication techniques. A 1 μm layer of Silicon dioxide ($SiO_2$) was thermally grown on the surface of a 4 inch Silicon (Si) wafer. HDMS resist SPR 700-1.2 (Microfabrication Materials Technologies, USA) was spun on at 4000 RPM and then the wafer was baked on a hot plate at 100° C. for 1 min (Maximus 804, SSE, Germany). The wafer was exposed using vacuum contact, 140 mJ $cm^{-2}$ (Karl Suss mask aligner, Karl Suss, Germany). Development was done in CD46 for 40 s, following a hard-bake at 110° C. for 1 min (Maximus). The oxide was etched using RIE (Applied Materials Precision 5000 mark II, Applied Materials, USA), followed by an isotropic Si etch for 10 s and an anisotropic Si etch for 20 cycles (Centura II (DPS & MxP) Applied Materials, USA). The wafer was passivated and a hydrophobic coating was generated by plasma deposition from $C_4F_8$ for 30 s in an inductively coupled plasma machine, ICP (ICP, STS, UK). The wafer was covered with dicing tape (SPS, Germany) before dicing. The chips were released from the tape and stored until usage upon which they were cleaned using acetone, isopropanol, water, and ethanol sequentially. All chemicals were purchased from Sigma-Aldrich, Sweden.

Preparation of Spider Silk Proteins:

Soluble silk proteins, non-functionalized spider silk ("4RepCT"; SEQ ID NO: 1), Z-functionalized spider silk (SEQ ID NO: 2) and $FN_{cc}$-functionalized spider silk (SEQ ID NO:3), purified from recombinant expression in *Escherichia coli*, at a final concentration of 3 mg mL-1 in 20 mM Tris (pH 8) were provided by Spider Technologies AB and stored at −20° C. until further use. For experiments with silk proteins in 20 mM $NH^4HCO^3$ (pH 8) and 20 mM $NaHCO^3$ (pH 8), the silk protein buffer was exchanged from Tris by dialysis.

Preparation of Coatings and Wires:

Coatings and wires were generated by ejecting a 5-10 μL hanging droplet of 0.1 mg $mL^{-1}$ Z-silk in 20 mM Tris buffer from a 0.4 mm syringe needle, followed by moving the droplet with respect to the pillar array surface. Two droplet movements were investigated, as illustrated in FIGS. 1A-1C: touch-and-release with the aim to form silk coatings only on the top of the pillars, in which the droplets were moved perpendicularly in contact with the surface, and immediately removed; and lateral droplet movement with the aim to form nanowires, in which the droplets were rolled horizontally over the pillar array. Lateral droplet movements (FIG. 1B) were performed by placing the surface horizontally on a motorized linear stage (NEMA 17 Stepper Motor MOX-02-30, Manufacturer, China); placing the syringe above the surface; ejecting a droplet from the syringe needle; and moving the stage with a speed of 0.1, 0.5, 1, 5 or 10 mm $s^{-1}$. Perpendicular touch-and-release droplet movements (FIG. 1A) were performed manually.

Once the droplet had been removed from the surfaces, they were subsequently washed with 20 mM Tris twice and MilliQ water once; incubated for 30 minutes in 0.005 mg $mL^{-1}$ IgG-Alexa Fluor 488 conjugate (rabbit source, Thermo Fisher Scientific) diluted in phosphate-buffered saline (PBS) supplemented with 0.05% Tween 20; and washed in PBS with 0.05% Tween 20 twice, and in PBS and MilliQ water once, after which they were blow-dried with an air gun. All experiments were performed in triplicate.

The adherence of the coatings to the superhydrophobic substrate was investigated by taking fluorescence images before and after submersion in water for 1, 2, 8, 24, and 48 hours. The samples were re-incubated in IgG-Alexa Fluor 488 conjugate after submersion and were washed as described above. The water that the coated substrates had been incubated in was evaporated on microscope glass slides. The adherence of the wires to the superhydrophobic substrate was investigated by taking fluorescence images before and after submersion in water for 48 hours as well as sonication (EMAG Emmi-12 HC, EMAG, Germany) for 10 minutes. The water that the substrates with wires had been sonicated in was evaporated on microscope glass slides. Wires were transferred from the superhydrophobic substrate to a flat OSTE220 (Mercene Labs, Sweden) substrate by immediately after lateral movement of the silk droplet, washing the superhydrophobic substrate in 20 mM Tris once and then pressing the surfaces together. The surfaces were then incubated in IgG-Alexa Fluor 488 conjugate and washed as described above.

Preparation of Sheets:

Sheets of silk were generated using drop casting of solutions of 0.3 mg $mL^{-1}$ and 3.0 mg $mL^{-1}$ $FN_{cc}$-silk or non-functionalized silk in either 20 mM Tris, $NH_4HCO_3$ or $NaHCO_3$ buffer. 20 μL droplets were evaporated on flat or superhydrophobic surfaces for 24 hours under either ambient conditions (35% relative humidity at 22° C.) or high humidity conditions (90% relative humidity at 22° C.). Thereafter, the surfaces were washed in water. Sheets were incubated in 0.1% Rhodamine B, diluted in water, for 30 minutes before washed three times in PBS.

The adherence of the sheets to the surface was investigated by first trying to remove the sheets in dry condition and then after submersion in water for 1, 2, 8, 24, and 48 hours. The water insolubility of the sheets was investigated by submerging them in water for 24 hours and taking fluorescence images of the sheets before and after submersion; and by submersion in complete endothelial cell media (PromoCell GmbH, Germany) for over 7 days.

Characterization:

The contact and roll-off angle of the surfaces were measured using a goniometer (ThetaLite, Biolin Scientific, Sweden). Coatings and wires were evaluated using fluorescence microscopy (Nikon Microphot-FXA, Nikon, USA). For the lateral movement experiments, images were captured in the center of the path. For the drop-and-remove experiments, images were centered on the droplet-array contact area. Different magnifications were used for the different pillar sizes: for pillar diameters d=15 and 20 μm 10×, for d=10 μm 20×; and for d=5 μm 40×. All images were analyzed in MATLAB (R2016a). For images where no wires were present, the intensity distribution between and across the pillars was measured and compared. For images where wires were present, wires were counted using an image processing algorithm.

Additionally, nanowire structures were evaluated using Scanning Electron Microscopy (SEM) (Gemini Ultra 55, Zeiss, Germany), where top images were taken along the droplet path to measure the diameter of the wire and tilted images to reveal information about the top coating. SEM images and AFM (Dimension Icon, Bruker, USA) images were also taken of the coatings. The water that the coatings and sheets had been incubated in was studied, after evaporation on a glass slide, using fluorescence microscopy and SEM.

The sheets were characterized by their appearance, their average size (defined as the average between the largest and smallest lateral distance), and their ability to be removed from the surface either before or after submersion in water. The surface roughness, internal structure, and thickness were studied using SEM and confocal microscopy (Olympus FV1000, Olympus, Japan).

To further study the wire generation process, a small droplet of 0.1 mg mL-1 Z-silk in 20 mM Tris buffer (around 2 μL) was placed on a surface and the evaporation process was recorded using an optical microscope (Nikon Optiphot, Nikon, USA) with a camera (MU503-CK, AmScope, USA).

The invention claimed is:

1. A method for manufacturing shaped polymers of silk proteins, comprising the steps of:
   a) depositing an aqueous solution of the silk proteins on a surface, wherein the aqueous solution of the silk proteins is deposited in the form of a droplet, and wherein the surface is a hydrophobic micropatterned surface adapted to prevent the aqueous solution from penetrating into the pattern and to receive the droplet of the aqueous solution of the silk proteins and retain its droplet state, and wherein the hydrophobic micropatterned surface is a superhydrophobic micropatterned surface having a contact angle of water of 90° or larger; and
   b) forming shaped polymers of the silk proteins on the surface.

2. The method according to claim 1, wherein the silk proteins are spider silk proteins.

3. The method according to claim 1, wherein the silk proteins are further containing a functional moiety.

4. The method according to claim 1, wherein the depositing of step a) is achieved by a motion of the droplet towards the surface along a direction intersecting the plane of the surface.

5. The method according to claim 4, wherein the depositing of step a) is achieved by an essentially perpendicular motion of the droplet in relation to the plane of the surface.

6. The method according to claim 1, wherein the forming of step b) comprises removing the deposited droplet from the surface by a motion of the droplet away from the surface along a direction intersecting the plane of the surface.

7. The method according to claim 6, wherein the deposited droplet is removed from the surface by an essentially perpendicular motion of the droplet in relation to the plane of the surface.

8. The method according to claim 6, wherein the forming of step b) comprises moving the deposited droplet laterally on the surface prior to its removal.

9. The method according to claim 8, wherein the droplet moving speed (s) is in the range of 0.1-10 mm $s^{-1}$.

10. The method according to claim 9, wherein the droplet moving speed is approximately 5 mm $s^{-1}$.

11. The method according to claim 1, wherein the forming of step b) involves evaporating the deposited droplet in its intact state on the surface.

12. The method according to claim 1, wherein the superhydrophobic micropatterned surface has a contact angle of water of 100° or larger.

13. The method according to claim 12, wherein the superhydrophobic micropatterned surface has a contact angle of water of 120°.

14. The method according to claim 12, wherein the superhydrophobic micropatterned surface has a contact angle of water of 150°.

15. The method according to claim 1, wherein the hydrophobic micropatterned surface includes protruding elements interspaced by a distance i of 1-100 μm, and wherein the protruding elements have a largest lateral extension d of 1-100 μm.

16. The method according to claim 15, wherein the protruding elements have a largest lateral extension d of 1-50 μm.

17. The method according to claim 16, wherein the protruding elements have a largest lateral extension d of 5-30 μm.

18. The method according to claim 15, wherein the interspace distance i between the protruding elements is 1-50 μm.

19. The method according to claim 18, wherein the interspace distance i between the protruding elements is 5-30 μm.

20. The method according to claim 15, wherein the protruding elements are pillar-shaped, and wherein the largest lateral extension d is the largest diameter of the pillars.

21. The method according to claim 1, wherein the hydrophobic micropatterned surface comprises silicon.

22. The method according to claim 1, wherein the hydrophobic micropatterned surface comprises an outer layer of a hydrophobic coating material.

23. The method according to claim 22, wherein the hydrophobic coating material is a perfluorocarbon compound.

24. The method according to claim 1, further comprising the step of:

c) removing the shaped polymers of the silk protein from the surface.

\* \* \* \* \*

```
                        SEQUENCE LISTING

<160> NUMBER OF SEQ ID NOS: 17

<210> SEQ ID NO 1
<211> LENGTH: 263
<212> TYPE: PRT
<213> ORGANISM: Euprosthenops australis
<220> FEATURE:
<221> NAME/KEY: DOMAIN
<222> LOCATION: (1)..(158)
<223> OTHER INFORMATION: REP fragment
<220> FEATURE:
<221> NAME/KEY: DOMAIN
<222> LOCATION: (159)..(165)
<223> OTHER INFORMATION: Spacer fragment
<220> FEATURE:
<221> NAME/KEY: DOMAIN
<222> LOCATION: (166)..(263)
<223> OTHER INFORMATION: CT fragment

<400> SEQUENCE: 1

Gly Pro Asn Ser Gly Gln Gly Gly Tyr Gly Gly Leu Gly Gln Gly Gly
1               5                   10                  15

Tyr Gly Gln Gly Ala Gly Ser Ser Ala Ala Ala Ala Ala Ala Ala Ala
                20                  25                  30

Ala Ala Ala Ala Gly Gly Gln Gly Gly Gln Gly Gln Gly Gly Tyr Gly
            35                  40                  45

Gln Gly Ser Gly Gly Ser Ala Ala Ala Ala Ala Ala Ala Ala Ala Ala
        50                  55                  60

Ala Ala Ala Ala Ala Gly Arg Gly Gln Gly Gly Tyr Gly Gln Gly Ser
65                  70                  75                  80

Gly Gly Asn Ala Ala Ala Ala Ala Ala Ala Ala Ala Ala Ala Ala Ala
                85                  90                  95

Ala Ala Gly Gln Gly Gly Gln Gly Gly Tyr Gly Arg Gln Ser Gln Gly
            100                 105                 110

Ala Gly Ser Ala Ala Ala Ala Ala Ala Ala Ala Ala Ala Ala Ala Ala
        115                 120                 125

Ala Gly Ser Gly Gln Gly Gly Tyr Gly Gly Gln Gly Gln Gly Gly Tyr
    130                 135                 140

Gly Gln Ser Ser Ala Ser Ala Ser Ala Ala Ala Ser Ala Ala Ser Thr
145                 150                 155                 160

Val Ala Asn Ser Val Ser Arg Leu Ser Ser Pro Ser Ala Val Ser Arg
                165                 170                 175

Val Ser Ser Ala Val Ser Ser Leu Val Ser Asn Gly Gln Val Asn Met
            180                 185                 190

Ala Ala Leu Pro Asn Ile Ile Ser Asn Ile Ser Ser Ser Val Ser Ala
        195                 200                 205

Ser Ala Pro Gly Ala Ser Gly Cys Glu Val Ile Val Gln Ala Leu Leu
    210                 215                 220

Glu Val Ile Thr Ala Leu Val Gln Ile Val Ser Ser Ser Ser Val Gly
225                 230                 235                 240

Tyr Ile Asn Pro Ser Ala Val Asn Gln Ile Thr Asn Val Val Ala Asn
                245                 250                 255

Ala Met Ala Gln Val Met Gly
            260
```

<210> SEQ ID NO 2
<211> LENGTH: 339
<212> TYPE: PRT
<213> ORGANISM: Artificial Sequence
<220> FEATURE:
<223> OTHER INFORMATION: Fusion protein

<400> SEQUENCE: 2

```
Met Gly Ser Ser Gly His His His His His Met Val Asp Asn Lys
1               5                   10                  15

Phe Asn Lys Glu Gln Gln Asn Ala Phe Tyr Glu Ile Leu His Leu Pro
                20                  25                  30

Asn Leu Asn Glu Glu Gln Arg Asn Ala Phe Ile Gln Ser Leu Lys Asp
            35                  40                  45

Asp Pro Ser Gln Ser Ala Asn Leu Leu Ala Glu Ala Lys Lys Leu Asn
65          70                      75                  80

Asp Ala Gln Ala Pro Lys Leu Glu Ala Leu Phe Gln Gly Pro Asn Ser
65          70                      75                  80

Gly Gln Gly Gly Tyr Gly Gly Leu Gly Gln Gly Gly Tyr Gly Gln Gly
                85                  90                  95

Ala Gly Ser Ser Ala Ala Ala Ala Ala Ala Ala Ala Ala Ala Ala Ala
                100                 105                 110

Gly Gly Gln Gly Gly Gln Gly Gln Gly Gly Tyr Gly Gln Gly Ser Gly
                115                 120                 125

Gly Ser Ala Ala Ala Ala Ala Ala Ala Ala Ala Ala Ala Ala Ala Ala
                130                 135                 140

Ala Gly Arg Gly Gln Gly Gly Tyr Gly Gln Gly Ser Gly Gly Asn Ala
145                 150                 155                 160

Ala Ala Ala Ala Ala Ala Ala Ala Ala Ala Ala Ala Ala Ala Gly Gln
                165                 170                 175

Gly Gly Gln Gly Gly Tyr Gly Arg Gln Ser Gln Gly Ala Gly Ser Ala
                180                 185                 190

Ala Ala Ala Ala Ala Ala Ala Ala Ala Ala Ala Ala Ala Gly Ser Gly
                195                 200                 205

Gln Gly Gly Tyr Gly Gly Gln Gly Gly Gly Tyr Gly Gln Ser Ser
            210                 215                 220

Ala Ser Ala Ser Ala Ala Ala Ser Ala Ala Ser Thr Val Ala Asn Ser
225                 230                 235                 240

Val Ser Arg Leu Ser Ser Pro Ser Ala Val Ser Arg Val Ser Ser Ala
                245                 250                 255

Val Ser Ser Leu Val Ser Asn Gly Gln Val Asn Met Ala Ala Leu Pro
                260                 265                 270

Asn Ile Ile Ser Asn Ile Ser Ser Val Ser Ala Ser Ala Pro Gly
                275                 280                 285

Ala Ser Gly Cys Glu Val Ile Val Gln Ala Leu Leu Glu Val Ile Thr
                290                 295                 300

Ala Leu Val Gln Ile Val Ser Ser Ser Val Gly Tyr Ile Asn Pro
305                 310                 315                 320

Ser Ala Val Asn Gln Ile Thr Asn Val Val Ala Asn Ala Met Ala Gln
                325                 330                 335

Val Met Gly
```

<210> SEQ ID NO 3
<211> LENGTH: 276

```
<212> TYPE: PRT
<213> ORGANISM: Artificial Sequence
<220> FEATURE:
<223> OTHER INFORMATION: Fusion protein
<220> FEATURE:
<221> NAME/KEY: DISULFID
<222> LOCATION: (5)..(14)

<400> SEQUENCE: 3

Gly Pro Asn Ser Cys Thr Gly Arg Gly Asp Ser Pro Ala Cys Pro Asn
1               5                   10                  15

Ser Gly Gln Gly Gly Tyr Gly Gly Leu Gly Gln Gly Tyr Gly Gln
            20                  25                  30

Gly Ala Gly Ser Ser Ala Ala Ala Ala Ala Ala Ala Ala Ala Ala
        35                  40                  45

Ala Gly Gly Gln Gly Gly Gln Gly Gln Gly Gly Tyr Gly Gln Gly Ser
        50                  55                  60

Gly Gly Ser Ala Ala Ala Ala Ala Ala Ala Ala Ala Ala Ala Ala
65                  70                  75                  80

Ala Ala Gly Arg Gly Gln Gly Gly Tyr Gly Gln Gly Ser Gly Gly Asn
                85                  90                  95

Ala Ala Ala Ala Ala Ala Ala Ala Ala Ala Ala Ala Ala Ala Gly
                100                 105                 110

Gln Gly Gly Gln Gly Gly Tyr Gly Arg Gln Ser Gln Gly Ala Gly Ser
            115                 120                 125

Ala Ala Ala Ala Ala Ala Ala Ala Ala Ala Ala Ala Ala Gly Ser
            130                 135                 140

Gly Gln Gly Gly Tyr Gly Gly Gln Gly Gln Gly Gly Tyr Gly Gln Ser
145                 150                 155                 160

Ser Ala Ser Ala Ser Ala Ala Ala Ser Ala Ala Ser Thr Val Ala Asn
                165                 170                 175

Ser Val Ser Arg Leu Ser Ser Pro Ser Ala Val Ser Arg Val Ser Ser
            180                 185                 190

Ala Val Ser Ser Leu Val Ser Asn Gly Gln Val Asn Met Ala Ala Leu
            195                 200                 205

Pro Asn Ile Ile Ser Asn Ile Ser Ser Val Ser Ala Ser Ala Pro
    210                 215                 220

Gly Ala Ser Gly Cys Glu Val Ile Val Gln Ala Leu Leu Glu Val Ile
225                 230                 235                 240

Thr Ala Leu Val Gln Ile Val Ser Ser Ser Val Gly Tyr Ile Asn
                245                 250                 255

Pro Ser Ala Val Asn Gln Ile Thr Asn Val Val Ala Asn Ala Met Ala
                260                 265                 270

Gln Val Met Gly
            275

<210> SEQ ID NO 4
<211> LENGTH: 98
<212> TYPE: PRT
<213> ORGANISM: Euprosthenops australis

<400> SEQUENCE: 4

Ser Arg Leu Ser Ser Pro Ser Ala Val Ser Arg Val Ser Ser Ala Val
1               5                   10                  15

Ser Ser Leu Val Ser Asn Gly Gln Val Asn Met Ala Ala Leu Pro Asn
            20                  25                  30

Ile Ile Ser Asn Ile Ser Ser Val Ser Ala Ser Ala Pro Gly Ala
```

```
                35                  40                  45
Ser Gly Cys Glu Val Ile Val Gln Ala Leu Leu Glu Val Ile Thr Ala
 50                  55                  60
Leu Val Gln Ile Val Ser Ser Ser Val Gly Tyr Ile Asn Pro Ser
 65                  70                  75                  80
Ala Val Asn Gln Ile Thr Asn Val Val Asn Ala Met Ala Gln Val
                 85                  90                  95
Met Gly

<210> SEQ ID NO 5
<211> LENGTH: 93
<212> TYPE: PRT
<213> ORGANISM: Araneus ventricosus

<400> SEQUENCE: 5

Asn Arg Leu Ser Ser Ala Glu Ala Ala Ser Arg Val Ser Ser Asn Ile
 1               5                  10                  15
Ala Ala Ile Ala Ser Gly Gly Ala Ser Ala Leu Pro Ser Val Ile Ser
                20                  25                  30
Asn Ile Tyr Ser Gly Val Val Ala Ser Gly Val Ser Ser Asn Glu Ala
                35                  40                  45
Leu Ile Gln Ala Leu Leu Glu Leu Leu Ser Ala Leu Val His Val Leu
 50                  55                  60
Ser Ser Ala Ser Ile Gly Asn Val Ser Ser Val Gly Val Asp Ser Thr
 65                  70                  75                  80
Leu Asn Val Val Gln Asp Ser Val Gly Gln Tyr Val Gly
                85                  90

<210> SEQ ID NO 6
<211> LENGTH: 5
<212> TYPE: PRT
<213> ORGANISM: Homo sapiens

<400> SEQUENCE: 6

Ile Lys Val Ala Val
 1               5

<210> SEQ ID NO 7
<211> LENGTH: 5
<212> TYPE: PRT
<213> ORGANISM: Homo sapiens

<400> SEQUENCE: 7

Tyr Ile Gly Ser Arg
 1               5

<210> SEQ ID NO 8
<211> LENGTH: 5
<212> TYPE: PRT
<213> ORGANISM: Homo sapiens

<400> SEQUENCE: 8

Glu Pro Asp Ile Met
 1               5

<210> SEQ ID NO 9
<211> LENGTH: 5
<212> TYPE: PRT
<213> ORGANISM: Homo sapiens

<400> SEQUENCE: 9
```

Asn Lys Asp Ile Leu
1               5

<210> SEQ ID NO 10
<211> LENGTH: 5
<212> TYPE: PRT
<213> ORGANISM: Homo sapiens

<400> SEQUENCE: 10

Gly Arg Lys Arg Lys
1               5

<210> SEQ ID NO 11
<211> LENGTH: 15
<212> TYPE: PRT
<213> ORGANISM: Homo sapiens

<400> SEQUENCE: 11

Lys Tyr Gly Ala Ala Ser Ile Lys Val Ala Val Ser Ala Asp Arg
1               5                   10                  15

<210> SEQ ID NO 12
<211> LENGTH: 12
<212> TYPE: PRT
<213> ORGANISM: Homo sapiens

<400> SEQUENCE: 12

Asn Gly Glu Pro Arg Gly Asp Thr Tyr Arg Ala Tyr
1               5                   10

<210> SEQ ID NO 13
<211> LENGTH: 11
<212> TYPE: PRT
<213> ORGANISM: Homo sapiens

<400> SEQUENCE: 13

Pro Gln Val Thr Arg Gly Asp Val Phe Thr Met
1               5                   10

<210> SEQ ID NO 14
<211> LENGTH: 12
<212> TYPE: PRT
<213> ORGANISM: Homo sapiens

<400> SEQUENCE: 14

Ala Val Thr Gly Arg Gly Asp Ser Pro Ala Ser Ser
1               5                   10

<210> SEQ ID NO 15
<211> LENGTH: 8
<212> TYPE: PRT
<213> ORGANISM: Homo sapiens

<400> SEQUENCE: 15

Thr Gly Arg Gly Asp Ser Pro Ala
1               5

<210> SEQ ID NO 16
<211> LENGTH: 10
<212> TYPE: PRT
<213> ORGANISM: Artificial Sequence
<220> FEATURE:
<223> OTHER INFORMATION: Modified from Homo sapiens
<220> FEATURE:
<221> NAME/KEY: DISULFID

```
<222> LOCATION: (1)..(10)

<400> SEQUENCE: 16

Cys Thr Gly Arg Gly Asp Ser Pro Ala Cys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: cell-binding peptide
<220> FEATURE:
<221> NAME/KEY: misc_feature
<223> OTHER INFORMATION: X = any amino acid other than Cys
<220> FEATURE:
<221> NAME/KEY: DISULFID
<222> LOCATION: (1)..(10)

<400> SEQUENCE: 17

Cys Xaa Xaa Arg Gly Asp Xaa Xaa Xaa Cys
1               5                   10
```